(12) United States Patent
Farooq et al.

(10) Patent No.: US 8,949,082 B2
(45) Date of Patent: Feb. 3, 2015

(54) HEALTHCARE INFORMATION TECHNOLOGY SYSTEM FOR PREDICTING OR PREVENTING READMISSIONS

(75) Inventors: Faisal Farooq, Norristown, PA (US); Romer E. Rosales, Downington, PA (US); Shipeng Yu, Exton, PA (US); Balaji Krishnapuram, King of Prussia, PA (US); Bharat R. Rao, Berwyn, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 740 days.

(21) Appl. No.: 13/153,551

(22) Filed: Jun. 6, 2011

(65) Prior Publication Data

US 2011/0295622 A1 Dec. 1, 2011

Related U.S. Application Data

(60) Continuation-in-part of application No. 12/488,083, filed on Jun. 19, 2009, which is a division of application No. 10/287,055, filed on Nov. 4, 2002, now Pat. No. 7,617,078.

(Continued)

(51) Int. Cl.
*G06F 7/60* (2006.01)
*G06F 17/10* (2006.01)
*G06F 19/00* (2011.01)
(Continued)

(52) U.S. Cl.
CPC .......... *G06F 19/3431* (2013.01); *G06F 19/322* (2013.01); *G06F 19/327* (2013.01); *G06F 19/3443* (2013.01); *G06Q 10/10* (2013.01); *G06Q 50/24* (2013.01)

USPC ............................................. 703/2

(58) Field of Classification Search
CPC ........... G06F 17/5018; G06F 17/5036; G06F 17/5009; G06F 2217/16; G06F 19/00; G06F 19/30; G06F 19/24; G06F 19/26; G06F 19/28; G06F 19/322; G06F 19/34; G06F 19/3431; G05B 17/02
USPC ............................................. 703/2
See application file for complete search history.

(56) References Cited

U.S. PATENT DOCUMENTS 5,486,999 A 1/1996 Mebane
5,738,102 A 4/1998 Lemelson
(Continued)

OTHER PUBLICATIONS

Philbin et al. "Prediction of Hospital Readmission for Heart Failure: Development of a Simple Risk Score Based on Administrative Data" Journal of the American College of Cardiology vol. 33, No. 6, 1999.*
(Continued)

*Primary Examiner* — Saif Alhija
(74) *Attorney, Agent, or Firm* — Joshua B Ryan (57) ABSTRACT

Hospital readmissions may be prevented. Readmission is prevented by predicting the probability of a given patient to be readmitted. The probability alone may prevent readmission by educating the patient or medical professional. The probability may be predicted during a patient stay and used to generate a workflow action item to reduce the probability, to warn, to output appropriate instructions, and/or assist in avoiding readmission. The probability may be specific to a hospital, physician group, or other entity, allowing prevention to focus on past readmission causes for the given entity.

20 Claims, 4 Drawing Sheets

Related U.S. Application Data (60) Provisional application No. 60/335,542, filed on Nov. 2, 2001, provisional application No. 61/352,515, filed on Jun. 8, 2010, provisional application No. 61/352,509, filed on Jun. 8, 2010.

(51) Int. Cl.
  *G06Q 10/10* (2012.01)
  *G06Q 50/24* (2012.01)

(56) References Cited

U.S. PATENT DOCUMENTS

| | | |
|---|---|---|
| 5,935,060 A | 8/1999 | Iliff |
| 6,056,690 A | 5/2000 | Roberts |
| 6,067,466 A | 5/2000 | Selker et al. |
| 6,081,786 A | 6/2000 | Barry et al. |
| 6,212,526 B1 | 4/2001 | Chaudhuri et al. |
| 6,302,844 B1 | 10/2001 | Walker et al. |
| 6,468,210 B1 | 10/2002 | Iliff |
| 6,523,019 B1 | 2/2003 | Borthwick |
| 6,551,243 B2 | 4/2003 | Bocionek et al. |
| 6,551,266 B1 | 4/2003 | Davis, Jr. |
| 6,587,829 B1 | 7/2003 | Camarda et al. |
| 6,641,532 B2 | 11/2003 | Iliff |
| 6,903,194 B1 | 6/2005 | Sato et al. |
| 7,130,457 B2 | 10/2006 | Kaufman et al. |
| 7,617,078 B2 | 11/2009 | Rao et al. |
| 2002/0029157 A1 | 3/2002 | Marchosky |
| 2002/0077756 A1 | 6/2002 | Arouh et al. |
| 2003/0036683 A1* | 2/2003 | Kehr et al. ............ 600/300 |
| 2003/0046114 A1 | 3/2003 | Davies et al. |
| 2003/0120133 A1 | 6/2003 | Rao et al. |
| 2003/0120134 A1 | 6/2003 | Rao et al. |
| 2003/0120458 A1 | 6/2003 | Rao et al. |
| 2003/0120514 A1 | 6/2003 | Rao et al. |
| 2003/0125984 A1 | 7/2003 | Rao et al. |
| 2003/0125985 A1 | 7/2003 | Rao et al. |
| 2003/0125988 A1 | 7/2003 | Rao et al. |
| 2003/0126101 A1 | 7/2003 | Rao et al. |
| 2003/0130871 A1 | 7/2003 | Rao et al. |
| 2004/0143462 A1 | 7/2004 | Hunt et al. |
| 2004/0158193 A1 | 8/2004 | Bui et al. |
| 2004/0167804 A1 | 8/2004 | Simpson et al. |
| 2004/0172297 A1 | 9/2004 | Rao et al. |
| 2005/0234740 A1 | 10/2005 | Krishnan et al. |
| 2007/0174086 A1 | 7/2007 | Walker |
| 2008/0275731 A1 | 11/2008 | Rao et al. |
| 2009/0171163 A1 | 7/2009 | Mates et al. |
| 2009/0319295 A1 | 12/2009 | Kass-Hout et al. |

OTHER PUBLICATIONS

Stephen F. Jencks, MD., M.P.H., et al., "Rehospitalizations among Patents in the Medicare Fee-for-Service Program," The New England Journal of Medicine, pp. 1418-1428, Apr. 2009.

Report to Congress, "Promoting Greater Efficiency in Medicare," MedPac, pp. 288, Jun. 2007.

Eleanor Herriman, et al., "Patient Non-adherence—Pervasiveness, Drivers, and Interventions," Sciences Spotlight Series, vol. 2, No. 4, Aug. 2007.

Cook, et al., "The Importance of medication adherence: from the doctor patient interaction to impact on health outcomes," The Forum 10, Oct. 13-15, 2010.

Gordon K. Norman, "It Takes More than Wireless to Unbind Healthcare," Presentation at Healthcare Unbound 2007 Conference (Abstract).

Lee Jacobs, "Are Your Patients Taking What You Prescribe? A Major Determinant: Clinician-Patient Communication," Physician Work Environment, vol. 6, No. 3, Summer 2002.

Michael P. Ho et al., "Impact of Medication Therapy Discontinuation on Mortality After Myocardial Infarction," Archives of Internal Medicine, 166: 1842-1847, 2007 (Abstract only).

Sergio B. Wey, et al., "Risk Factors for Hospital-Acquired Candidemia," A Matched Case Control Study, Archives of Internal Medicine, 1989;149(10), (abstract only).

Andrew Pollack, "Rising Threat of Infections Unfazed by Antibiotics," New York Times, Feb. 27, 2010.

http://en.wikipedia.org/wiki/Nosocomial infection, downloaded Jun. 2, 2011.

Janice Morse, "Preventing Patient Falls," Sage Publications, 1997.

Ann Hendrich, "How to Try This: Predicting Patient Falls," American Journal of Nursing, Nov. 2007, vol. 107, No. 11, pp. 50-58.

Kamp, et al. "Database system support for multidimensional data analysis in environmental epidemiology", The 1997 International Database Engineering & Applications Symposium; Montreal; Can; Aug. 25-27, 1997. pp. 180-188. 1997.

King, et al., "MEDUS/A: Distributing Database Management for Medical Research", Proceedinngs of Computer Networks Compcon 82, 20.09.1982-23.09.1982 pp. 635-642.

Boxwala et al, "Architecture for a Multipurpose Guideline Execution Engine", Proc. AMIA Symp 1999, pp. 701-705.

"Guidance for Institutional Review Boards and Clinical Investigators 1998 Update", Sep. 1998, U.S. Food and Drug Administration, http://www.fda.gov/ScienceResearch/SpecialTopics/RunningClinicalTrials/GuidancesInformationSheetsandNotices/ucm113793.htm#IRBMember.

Kassirer, "The Use and Abuse of Practice Profiles", The New England Journal of Medicine, vol. 330:634-636, Mar. 3, 1994.

Chen, et al., Do "America's Best Hospitals" Perform Better for Acute Myocardial Infarction?, The New England Journal of Medicine, vol. 340, No. 4:286-292, Jan. 28, 1999.

Hofer, et al., "The Unreliability of Individual Physician 'Report Cards' for Assessing the Costs and Quality of Care of a Chronic Disease", JAMA, Jun. 9, 1999, vol. 281, No. 22, pp. 2098-2105.

Ong et al, "The Colorectal Cancer Recurrence Support (CARES) System; Artificial Intelligence in Medicine", Nov. 1997, Elsevier, Netherlands, vol. 11, pp. 175-188.

Nahm, et al., "A Mutually Beneficial Integration of Data Mining and Information Extraction", In Proceedings of the Seventeenth National Conference on Artificial Intelligence (AAAI-2000), Jul. 30, 2000, pp. 627-632, Austin, TX, 20001.

Rao, et al., "Data mining for disease management: adding value to patient records", Electromedica, vol. 68, 2000, pp. 63-67.

Mills, "Computer Technology of the Not-Too-Distant Future" Sep. 1993, Medical Laboratory Observer, vol. 25, No. 9, p. 78.

Duda, et al., "Pattern Classification—Chapter 1" 2001, John Wiley & Sons, New York, US, XP002536377, pp. 14-17.

Hudson, et al., "The Feasibility of Using Automated Data to Assess Guideline-Concordant Care for Schizophrenia", Journal of Medical Systems, vol. 23 No. 4 1999, pp. 299-307.

PR Newswire, "Diabetes Health Management Award Honors Mayo Clinic's Zimmerman", Sep. 25, 2000, http://www.thefreelibrary.com/Diabetes Health Management Award Honors Mayo Clinic's Zimmerman.-a065465402.

Hudson, Mary E., "CAATS and compliance—computer-assisted audit techniques in health care", Internal Auditor, Apr. 1998, vol. 55, No. 2, p. 25, http://findarticles.com/p/articlesimi_m4153/is_n2_v55/ai_20860208/.

Grimes, Seth, "Structure, Models and Meaning, Is 'Unstructured' data merely unmodeled?", Intelligent Enterprise, Mar. 2005, http://intelligent-enterprise.informationweek.com/showArticle.jhtml?articleID=59301538.

Berkus, "Unstructured Data as an Oxymoron", ITtoolbox Blogs, Sep. 1, 2005, http://it.toolbox.com/blogs/database-soup/unstructured-data-as-an-oxymoron-5588.

Larsen, "Fast and Effective Test Mining Using Linear-time Document Clustering", In Knowledge Discovery and Data . Mining (1999), pp. 16-22.

Rao, "From Unstructured Data to Actionable Intelligence", IT Pro, Nov./Dec. 2003, pp. 29-35.

Mitchell, "Machine Learning and Data Mining", Communications of the ACM, Nov. 1999, vol. 42, No. 11, pp. 31-36.

(56) References Cited

OTHER PUBLICATIONS

Kleissner, "Data Mining for the Enterprise", System Sciences, 1998, Proceedings of the Thirty-First Hawaii International Conference on Kohala Coast, HI, Jan. 6-9, 1998, IEEE Comput. Soc. US, pp. 295-304.

Evans, et al., "Using Data Mining to Characterize DNA Mutations by Patient Clinical Features", Proc AMIA Annu Fall Symp. 1997: 253-257.

Waltz, "Information Understanding Integrating Data Fusion and Data Mining Processes", Circuits and Systems, 1998, Proceedings of the 1998 IEEE International Symposium in Monterey, CA, USA, May 31-Jun. 3, 1998, NY, NY, May 31, 1998, pp. 553-556.

Roemer, et al., "Improved diagnostic and prognostic assessments using health management information fusion," Autotestcon Proceedings, 2001. IEEE Systems Readiness Technology Conference, vol., No., pp. 365-377, 2001.

Chemical and Biological Arms Control Institute: "Bioterrorism in the United States:Threat, Preparedness and Response", Contract No. 200*1999*00132, Nov. 2000.

Hanson, et al.. "Probabilistic Heuristic Estimates", Annals of Mathematics and Artificial Intelligence, vol. 2, Nos. 1-4, pp. 209-220, 1990.

Edward F. Philbin, et al., "Prediction of Hospital Readmission for Heart Failure: Development of a Simple Risk Score Based on Administrative Data", Journal of the American College of Cardiology, vol. 33, No. 6, 1999 pp. 1560-1566.

\* cited by examiner

HEALTHCARE INFORMATION TECHNOLOGY SYSTEM FOR PREDICTING OR PREVENTING READMISSIONS

RELATED APPLICATIONS

The present patent document is a continuation in-part of U.S. patent application Ser. No. 12/488,083, filed Jun. 19, 2009, which is a continuation of U.S. patent application Ser. No.: 10/287,055 filed Nov. 4, 2002, now U.S. Pat. No. 7,617, 078, which claims the benefit of the filing date of Provisional U.S Patent Application Ser. No. 60/335,542, and the present patent document claims the benefit of the filing date under 35 U.S.C. §119(c) of Provisional U.S. Patent Application Ser. Nos. 61/352,515, filed Jun. 8, 2010, and 61/352,509, filed Jun. 8, 2010, which are hereby incorporated by reference.

BACKGROUND

The present embodiments relate to predicting risk of hospital readmission and/or providing valuable information to potentially prevent readmission. Preventing readmission may reduce medical costs and benefit the patient and hospital.

In the United States, about 20% of all Medicare beneficiaries are readmitted, out of which 75% of the readmissions are potentially preventable. Examples of this include admission for angina following discharge for percutaneous transluminal coronary angioplasty (PTCA) or admission for trauma following discharge for Acute Myocardial Infarction (AMI). The government and other private payers are focusing on controlling the costs associated with readmission. Preventable readmission costs may amount to nearly $12 billion annually. The Center for Medicare and Medicaid Services (CMS) currently mandates public reporting of readmission rates and payers may institute financial penalties for poor performance and/or rewards for low readmissions.

With the recent stimulus and inevitable paradigm shift towards accountable care, organizations are focusing on cost reduction, standardized care, and quality improvement. There is a large, growing need to help hospitals reduce preventable rate of readmissions to improve quality of care and avoid financial and legal implications. Many of these preventable readmissions are caused by discrepancies in personal health records that have not been updated with previous or current admissions, medications (pre and post admission) not reconciled at the time of discharge, and no proper follow up with physicians or nurses.

SUMMARY

In various embodiments, systems, methods and computer readable media are provided for predicting hospital readmission. Readmission is prevented by predicting the probability of a given patient to be readmitted. The probability alone may prevent readmission by educating the patient or medical professional. The probability may be predicted at the time of discharge and used to generate a workflow action item to reduce the probability, to warn, to output appropriate discharge instructions, and/or assist in avoiding readmission. The probability may be specific to a hospital, physician group, or other entity, allowing prevention to focus on past readmission causes for the given entity.

In a first aspect, a method is provided for predicting hospital readmission. An indication of discharge of a patient from a medical entity is received. Application of a predictor of readmission is triggered in response to the receiving of the indication. The predictor of the readmission is applied to an electronic medical record of the patient in response to the triggering. The predictor is based on readmission data of the medical entity. A probability of readmission of the patient is predicted based on applying the predictor to the electronic medical record of the patient at discharge. An output is provided as a function of the probability.

In a second aspect, a system is provided for predicting hospital readmission. At least one memory is operable to store data for a plurality of readmitted patients of a first medical entity. A first processor is configured to: identify variables contributing to readmission for the first medical entity based on the data for the plurality of the readmitted patients of the first medical entity, and incorporate the variables into a predictor of readmission for a future patient of the first medical entity.

In a third aspect, a non-transitory computer readable storage medium has stored therein data representing instructions executable by a programmed processor for predicting hospital readmission. The storage medium includes instructions for predicting a probability of readmission of a patient, the predicting occurring at a time of discharge, comparing the probability to a threshold, and generating an alert based on the comparing, the generating occurring at the time of discharge.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

DESCRIPTION OF PREFERRED EMBODIMENTS

A majority of readmission cases may be prevented if the risk of the patient to be readmitted is established as early as possible. The risk of readmission is calculated from the patient records (e.g., clinical, financial and demographic). For medical entity specific readmission, the risk is calculated by a classifier based on past patient data for the medical institution. For a current patient, the system identifies whether the patient is at risk for readmission. The risk is automatically calculated using a predictive model. The possible reasons for risk of a particular patient may be identified, and a plan for mitigating the risk may be presented.

For generating the predictor from data of previous patients and for applying the predictor for a current patient, patient data is obtained from Electronic Medical Records (EMRs), such as patient information databases, Radiology Information Systems (RIS), Pharmacological Records, or other form of medical data storage or representation. In an EMR or RIS, various data elements are normally associated to a patient or patient visit, such as diagnosis codes, lab results, pharmacy, insurance, doctor notes, images, and genotypic information. Using the mined data, a computer system predicts the risk of readmissions of a patient upon discharge and suggests optimal plans to mitigate this risk.

The tasks for predicting the risk of readmission of a patient are automatically performed using this combination. Deviations and discrepancies may be identified, and mitigations to possibly prevent the readmission may be output.

The risk of readmission may be specific to a given medical entity. Any medical entity, such as a hospital, group of hospitals, group of physicians, region group (e.g., hospitals in a city, county, or state), office, insurance group, or other collection of medical professionals associated with patients, may contribute data to mitigation of risk of readmission. By using data associated with a specific medical entity, risk mitigation more focused on that entity rather than hospitals in general may be provided.

For example, a hospital may have a greater risk of readmission for infection than hospitals in a peer group. The data for patients previously admitted to the hospital is used to train a predictor. A machine learns the factors at that hospital contributing to the risk of readmission. Manually input factors may be included as well. The factors used, the relationship between factors, or relative weighting of the factors is specific to the hospital. Upon discharge of a later patient of the hospital, the risk of readmission may be predicted. Given the hospital specific predictor, appropriate mitigation may be provided in response to the prediction. Alerts and associated workflow actions may be output to reduce the risk of readmission for the patient.

Figure 1:
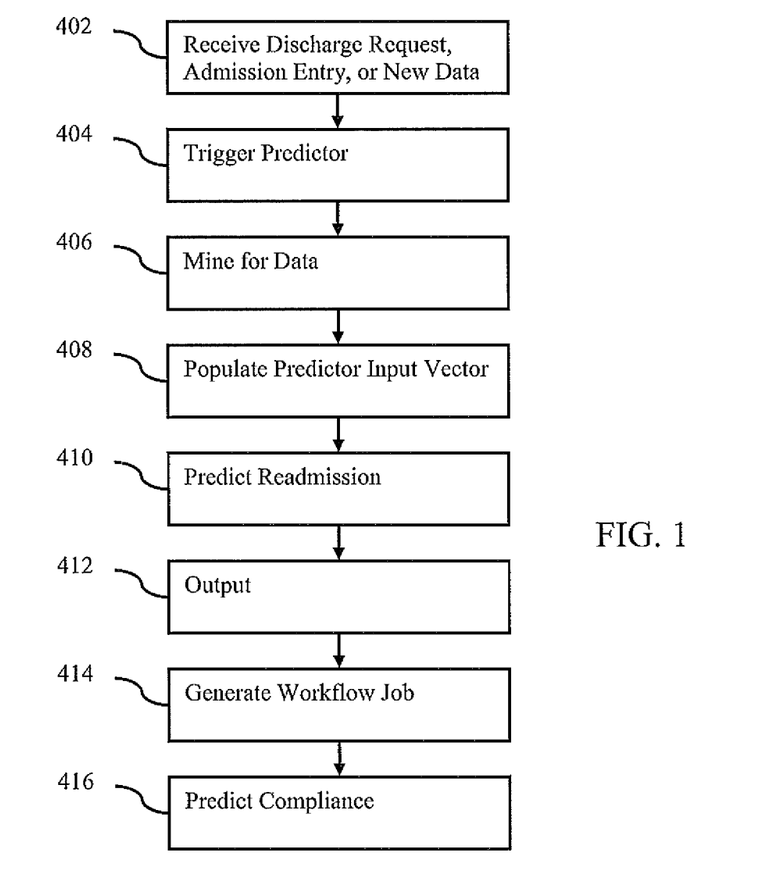
FIG. 1 is a flow chart diagram of one embodiment of a method for predicting readmission.

FIG. 1 shows a method for preventing hospital readmission. The method is implemented by or on a computer, server, processor, or other device. The method is provided in the order shown, but other orders may be provided. Additional, different or fewer acts may be provided. For example, acts 402, 404, 406, 408, 412, 414, 416, or combinations thereof are not provided. As another example, the mining for data of act 406 is not performed as another source of information for prediction is provided. In another example, act 416 is not provided.

Continuous (real time) or periodic prediction of the risk of readmission is performed. Throughout the hospital stay, the care provider may tune their care based on the most recent prediction. Given the rise in accountable care where the care provider shares the financial risk, prediction before scheduling discharge allows alteration of the care of the patient in such a way that the risk of readmission is kept low as the patient progresses on the floor. The risk may be predicted right at the time the patient is admitted and/or other times. As the time passes and as more data (e.g., new labs results, new medications, new procedures, existing history etc.) is gathered, the risk may be updated continously for the care provider to monitor.

In act 402, an indication of discharge of, admission of, or new data for a patient from a medical entity is received. The receipt is by a computer or processor. For example, a nurse or administrator enters data for the medical record of a patient indicating discharge. The entry may be doctor instructions to discharge, may be that the patient is being discharged, may be scheduling of a discharge, or may be another discharge related entry. As another example, a new data entry is provided in the electronic medical record of the patient. In another example, an assistant enters data showing admission or other key trigger event (e.g., completion of surgery, assignment of the patient to another care group, or a change in patient status). In alternative embodiments, the indication is not received.

In act 404, application of a predictor of readmission is triggered. The trigger is in response to the receiving of the indication. An automated workflow is started in response to receiving the indication. The entry of discharge, admission, or other information causes a processor to run a prediction process.

The workflow determines whether there is an avoidable chance of readmission or a probability of readmission above a norm for a patient. This workflow occurs in response to discharge or scheduling discharge, admission, or other event of the patient. The triggered workflow begins prior to, during or after patient discharge. In one embodiment, the trigger occurs, at least in part, in real-time with patient discharge scheduling. While the patient is in the hospital and after determining that the patient is ready for discharge, the workflow for readmission prediction is started. The workflow may be performed in real-time during the actual patient stay in other embodiments, such as at admission, periodically during a patient stay, or in response to other events or data entry. The prediction may be performed after actual discharge.

In other embodiments, the prediction of risk for readmission is triggered based on an event other than discharge. For example, one or more events identified as associated with readmission are used as a trigger. A clinical action, entry of medication or prescription, completion of surgery, or other entry or action triggers the application of the predictor for the patient. Where a given medical entity has a particular concern for readmission, such as caused by failure to reconcile prescriptions, activity related to that concern may trigger application (e.g., triggering when an indication that a medication has been prescribed). The triggering event may be different for different medical entities.

In act 406, the electronic medical record of the patient is mined. To predict the risk of readmission, information is gathered. The classifier for prediction has an input feature vector or group of variables used for prediction. The values for the variables for a particular patient are obtained by mining the electronic medical record for the patient.

The electronic medical record for the patient is a single database or a collection of databases. The record may include data at or from different medical entities, such as data from a database for a hospital and data from a database for a primary care physician whether affiliated or not with the hospital. Data for a patient may be mined from different hospitals. Different databases at a same medical entity may be mined, such as mining a main patient data system, a separate radiology system (e.g., picture archiving and communication system), a separate pharmacy system, a separate physician notes system, and/or a separate billing system. Different data sources for the same and/or different medical entities are mined.

The different data sources have a same or different format. The mining is configured for the formats. For example, one, more, or all of the data sources are of structured data. The data is stored as fields with defined lengths, text limitations, or other characteristics. Each field is for a particular variable. The mining searches for and obtains the values from the desired fields. As another example, one, more, or all of the data sources are of unstructured data. Images, documents (e.g., free text), or other collections of information without defined fields for variables is unstructured. Physician notes may be grammatically correct, but the punctuation does not define values for specific variables. The mining may identify a value for one or more variables by searching for specific criteria in the unstructured data.

Any now known or later developed mining may be used. For example, the mining is of structured information. A specific data source or field is searched for a value for a specific variable. As another example, the values for variables are inferred. The values for different variables are inferred by probabilistic combination of probabilities associated with different possible values from different sources. Each possible value identified in one or more sources are assigned a probability based on knowledge (statistically determined probabilities or professionally assigned probabilities). The possible value to use as the actual value is determined by probabilistic combination. The possible value with the highest probability is selected. The selected values are inferred values for the variables of the feature vector of the predictor of readmission.

U.S. Pat. No. 7,617,078, the disclosure of which is incorporated herein by reference, shows a patient data mining method for combining electronic medical records for drawing conclusions. This system includes extraction, combination and inference components. The data to be extracted is present in the hospital electronic medical records in the form of clinical notes, procedural information, history and physical documents, demographic information, medication records or other information. The system combines local and global (possibly conflicting) evidences from medical records with medical knowledge and guidelines to make inferences over time.

U.S. Published Application No. 2003/0120458, the disclosure of which is incorporated herein by reference, discloses mining unstructured and structured information to extract structured clinical data. Missing, inconsistent or possibly incorrect information is dealt with through assignment of probability or inference. These mining techniques are used for quality adherence (U.S. Published Application No. 2003/0125985), compliance (U.S. Published Application No. 2003/0125984), clinical trial qualification (U.S. Published Application No. 2003/0130871), and billing (U.S. Published Application No. 2004/0172297). The disclosures of the published applications referenced in the above paragraph are incorporated herein by reference. Other patent data mining for mining approaches may be used, such as mining from only structured information, mining without assignment of probability, or mining without inferring for inconsistent, missing or incorrect information. In alternative embodiments, values are input by a user for applying the predictor without mining.

In act 408, a feature vector used for predicting the probability is populated. By mining, the values for variables are obtained. The feature vector is a list or group of variables used to predict the likelihood of readmission. The mining outputs values for the feature vector. The output is in a structured format. The data from one or more data sources, such as an unstructured data source, is mined to determine values for specific variables. The values are in a structured format— values for defined fields are obtained.

The mining may provide all of the values, such as resolving any discrepancies based on probability. Any missing values may be replaced with an average or predetermined value. The user may be requested to enter a missing value or resolve a choice between possible values for a variable. Alternatively, missing values are not replaced where the predictor may operate with one or more of the values missing.

The feature vector is populated by assigning values to variables in a separate data storage device or location. A table formatted for use by the predictor is stored. Alternatively, the values are stored in the data sources from which they are mined and pointers indicate the location for application of the predictor.

In act 410, the probability of readmission is predicted by applying the predictor. The predictor is a classifier or model. In one embodiment, the predictor is a machine-trained classifier. Any machine training may be used, such as training a statistical model (e.g., Bayesian network). The machine-trained classifier is any one or more classifiers. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used. Error-correcting output code (ECOC) may be used. In one embodiment, the machine-trained classifier is a probabilistic boosting tree classifier. The detector is a tree-based structure with which the posterior probabilities of readmission are calculated from given values of variables. The nodes in the tree are constructed by a non-linear combination of simple classifiers using boosting techniques. The probabilistic boosting tree (PBT) unifies classification, recognition, and clustering into one treatment. Alternatively, a programmed, knowledge based, or other classifier without machine learning is used.

For learning-based approaches, the classifier is taught to distinguish based on features. For example, a probability model algorithm selectively combines features into a strong committee of weak learners based on values for available variables. As part of the machine learning, some variables are selected and others are not selected. Those variables with the strongest or sufficient correlation or causal relationship to readmission are selected and variables with little or no correlation or causal relationship are not selected. Features that are relevant to readmission are extracted and learned in a machine algorithm based on the ground truth of the training data, resulting in a probabilistic model. Any size pool of features may be extracted, such as tens, hundreds, or thousands of variables. The pool is determined by a programmer and/or may include features systematically determined by the machine. The training determines the most determinative features for a given classification and discards lesser or non-determinative features.

The classifier is trained from a training data set using a computer. To prepare the set of training samples, actual readmission is determined for each sample (e.g., for each patient represented in the training data set, whether or after how long readmission occurred is determined). Any number of medical records for past patients is used. By using example or training data for tens, hundreds, or thousands of examples with known readmission status, a processor may determine the interrelationships of different variables to the outcome of readmission. The training data is manually acquired or mining is used to determine the values of variables in the training data. The training may be based on various criteria, such as readmission within a time period.

The training data is for the medical entity for which the predictor will be applied. By using data for past patients of the same medical entity, the variables or feature vector most relevant to readmission for that entity are determined. Different variables may be used by a machine-trained classifier for one medical entity than for another medical entity. Some of the training data may be from patients of other entities, such as using half or more of the examples from other entities with similar readmission concerns, sizes, or patient populations. The training data from the specific institution may skew or still result in a different machine-learnt classifier for the entity than using fewer examples from the specific institution. In alternative embodiments, all of the training data is from other medical entities, or the predictor is trained in common for a plurality of different medical entities.

The classifier may be trained to predict based on different time periods, such as readmission within 30 days or after 1 year. In alternative embodiments, the predictor is programmed, such as using physician knowledge or the results of studies.

The classifier is trained to predict readmission in general. Alternatively, separate classifiers are trained for different reasons for readmission, such as training a classifier for readmission for trauma following discharge for acute myocardial infarction and another classifier for readmission for angina following discharge for precutaneous transluminal coronary angioplasty.

The learnt predictor is a matrix. The matrix provides weights for different variables of the feature vectors. The values for the feature vector are weighted and combined based on the matrix. The predictor is applied by inputting the feature vector to the matrix. Other representations than a matrix may be used.

For application, the predictor is applied to the electronic medical record of a patient. In response to the triggering, the values of the variables used by the learned classifier are obtained. The values are input to the predictor as the feature vector. The predictor outputs a probability of readmission of the patient based on the patient's current electronic medical record.

The probability of readmission is determined automatically. The user may input one or more values of variables into the electronic medical record, but the prediction is performed without entry of values after the trigger and while applying the predictor. Alternatively, one or more inputs are provided, such as resolving ambiguities in values or to select an appropriate classifier (e.g., select a predictor of readmission for infection as opposed to readmission for trauma).

By applying the predictor to mined information for a patient, a probability of readmission is predicted for that patient. The machine-learnt or other classifier outputs a statistical probability of readmission based on the values of the variables for the patient. Where the prediction occurs in response to an event, such as triggering at the request of a medical professional or administrator, the probability is predicted from that time.

The classifier may indicate one or more values contributing to the probability. For example, the failure to prescribe aspirin is identified as being the strongest link or contributor to a probability of readmission for a given patient being beyond a threshold. This variable and value are identified. The machine-learnt classifier may include statistics or weights indicating the importance of different variables to readmission and/or the normal. In combination with the values, some weighted values may more strongly determine an increased probability of readmission. Any deviation from norm may be highlighted. For example, a value or weighted value of a variable a threshold amount different from the norm or mean is identified. The difference alone or in combination with the strength of contribution to the probability is considered in selecting one or more values as more significant. The more significant value or values may be identified.

The prediction is made during the patient stay. The prediction may be repeated at different times during the patient stay. The prediction may be made at the time of discharge, such as the day of discharge. The prediction may be updated, such as made before discharge and updated after discharge based on any data entered after the original prediction.

The probability of readmission is compared to one or more thresholds to establish risk. The thresholds may be any probability based on national standards, local standards, or other criteria. The medical entity may set the thresholds to customize their definition of low, medium or high risk patients. For example, the medical entity sets a threshold to distinguish a probability of readmission that is unusually high for that medical entity, for a similar class of medical entities, for entities in a region, for a rate important to reimbursement, or other grouping or consideration.

The comparison may be used to identify a patient for which further action may help reduce the probability of readmission. The comparison may be used to place the patient in a range. The output probability value may be used to classify the patient into different subgroups, such as high, medium, or low risk of readmission.

In addition, appropriate quantification of severity (Low, Medium and High) may be used to reflect the stratification of risk. A different classifier or the same classifier weights the probability by the type of readmission. For more serious complications or reasons for readmission, a lesser probability may still be quantified as higher severity.

In alternative embodiments of creating and applying the predictor, the prediction of readmission is integrated as a variable to be mined. The inference component determines the probability based on combination of probabilistic factoids or elements. The probability of readmission is treated as part of the patient state to be mined. Domain knowledge determines the variables used for combining to output the probability of readmission.

An output is provided in act 412. The output is a function of the probability. The probability is used in a further workflow or output. For example, the probability causes a job or action item in a workflow in an effort to reduce the probability. As another example, the probability with or without identification of the most significantly contributing value or values and/or type of readmission predicted is used to recommend the type of follow-up, discharge instructions, or other clinical action.

This analysis may be performed in real time. If performed in real time, suggestions and/or corrections are output based on the probability. The suggestions and/or corrections may reduce the risk in a timely manner. Retrospective analysis may establish the top readmission reasons for the patients at a particular institution medical entity and possibly suggest alternative workflows based on best clinical practices.

In one embodiment, an alert is generated based on the comparing of the probability to the threshold or thresholds. The alert is generated during the patient stay, at the time of discharge (e.g., when a medical professional is preparing discharge papers), or other times.

The alert is sent via text, email, voice mail, voice response, or network notification. The alert indicates the level of risk of readmission, allowing mitigation when desired or appropriate. The alert is sent to the patient, family member, treating physician, nurse, primary care physician, and/or other medical professional. The alert may be transmitted to a computer, cellular phone, tablet, bedside monitor of the patient, or other device. The recipient of the alert may examine why the probability is beyond the threshold, determine changes in workflow to reduce the risk of readmission for other patients, and/or take actions to reduce the risk for the patient for which the alert was generated.

The alert indicates the patient and a risk of readmission. Other information may be provided alternatively or additionally, such as identification of one or more values and corresponding variables correlating with the severity or risk level.

In one embodiment, the alert is generated as a displayed warning while preventing entry of discharge or other information. The user is prevented from scheduling discharge or entering other data where the probability of readmission and/or severity of predicated readmission are sufficiently high. In response to the user attempting to schedule discharge or enter information associated with the patient, the alert is generated and the user is prevented from entering or saving the information. The prevention is temporary (e.g., seconds or minutes), may remain until the probability has been reduced or require an over-ride from an authorized personnel (e.g. a case manager or an attending physician). The prevention may be for one type of data entry (e.g., discharge scheduling) but allow another type (e.g., medication reconciliation) to reduce the risk of readmission.

A user may be requested to enter additional information to help improve readmissions rates in general, such as the user reconciling different prescriptions, scheduling a follow-up, resolving discrepancies in the electronic medical record, resolving a lack of adherence to a guideline, completing documentation in the electronic medical record, or arranging for a clinical action. The system may output a list of variables that can be considered to reduce the risk of readmission. At least one variable having a value for the patient associated with a strong, stronger, or strongest link to the probability is output. For example, a patient has an unusually high measured blood characteristic, indicating a possible infection. This high value may be the most significant reason for a probability of readmission above a threshold. Most significant or significant may be based on the weight for the variable and the value in determining the probability or be based on a combination of factors (e.g., the relative strength or weight and the amount of deviance from a threshold). The strength of the link may be relative to links for other values of other variables to the risk of readmission. The reasons for the risk of readmission are identified.

Recommendations may be made based on the identified variable, variables, or combination of variables. For example, based on the past and current medical records of a patient, it can be determined whether the personal health record of the patient has been updated or not with the current admission. Where the probability of readmission is based, at least in part, on old information, a recommendation to document or update the record is provided. Similarly, it can be highlighted whether the medications have been reconciled or not.

The recommendation is textual, such as providing instructions. Other recommendations may be visual. A visual representation of the relationship of the probability to the patient record may assist user understanding. The visual representation is output on a display or printed. The visual representation of the relationship links elements or factoids (variables) to the resulting risk of readmission. The values for the variables from a specific patient record are inserted. A pictorial representation of the contribution of different variables, based on the values, to the risk may assist the user in general understanding of how any conclusions are supported by inputs.

The visual representation shows the dependencies between the data and conclusions. The dependencies may be actual or imaginary. For example, a machine learning technique may be used. The relationship of a given input to the actual output may be unknown, but a statistical correlation may be identified by machine learning. To assist in user understanding, a relationship may be graphically represented without actual dependency, such as probability or relative weighting, being known.

The visual representation may have any number of inputs, outputs, nodes or links. The types of data are shown. The relative contribution of an input to a given output may be shown, such as colors, bold, or breadth of a link indicating a weight. The data source or sources used to determine the values of the variables may be shown (e.g., billing record, prescription database or others).

The probability of readmission and/or variables associated with the probability of readmission for a particular patient may be used to determine a mitigation plan. The mitigation plan includes instructions, prescriptions, education materials, schedules, clinical actions, or other information that may reduce the risk of readmission. The next recommended clinical actions or reminders for the next recommended clinical actions may be output so that health care personnel are better able to follow the recommendations.

A library of mitigation plans is provided. Separate plans may be provided for different reasons for possible readmission, different variables causing a higher risk of readmission, and/or different combinations of both. The plan or plans appropriate for a given patient are obtained and output.

The output may be based on a criteria set for the medical entity. For example, the medical entity may set the threshold for comparison to be more or less inclusive of different levels of risk. As another example, the medical entity may select a combination of factors to trigger an alert, such as probability level and types of variables contributing to the probability level. If one variable causes the predictor to regularly and inaccurately predict a risk higher than the threshold amount, then patients with higher probability based just or mostly on that variable may not have an alert output or a different alert may be output.

The output may be discharge instructions for the patient and/or medical professional (e.g., treating and/or primary care physician). The discharge instructions may include the mitigation plan. Alternatively or additionally, the discharge instructions include the predicted probability. Patients or physicians may be more likely to take corrective or preventative actions where the probability of readmission is known. The instruction may indicate the difference in probability if a value is changed and by how much, showing benefit to change in behavior or performance of clinical or medical action. Recommendations may be made to mitigate the risks. Semi-automated discharge instructions based on the longitudinal clinical record are created. In other embodiments, the output is a mitigation plan to be performed during the patient's stay.

An optimal follow-up strategy (e.g., phone call, in-home follow-up, or visit to a doctor) may be provided in the instructions. The follow-up strategy may be selected or determined based on the probability of readmission and/or the variables contributing to the probability of readmission being beyond the threshold. For example, an in-home follow-up is scheduled for a probability further beyond the threshold (e.g., beyond another threshold in a stratification of risk), and a phone call is scheduled for a probability closer to the threshold (e.g., for a lower risk). As another example, the severity of the type of readmission predicted is considered. The probability may be utilized to manage the care and suggest possible and alternative care plans for optimal patient outcomes.

In another embodiment, a job entry in a workflow is automatically scheduled as a function of the probability. A computerized workflow system includes action items to be performed by different individuals. The action items are communicated to the individual in a user interface for the workflow, by email, by text message, by placement in a calendar, or by other mechanism.

The workflow job is generated for a case manager. The job entry may be made to avoid readmission. The job entry may be to update patient data, arrange for clinical action, update a prescription, arrange for a prescription, review test results, arrange for testing, schedule a follow-up, review the probability, review patient data, or other action to reduce the probability of readmission. For example, where a follow-up is not scheduled during discharge and is not automatically arranged, arranging for the follow-up may be placed as an action item in an administrator's, assistant's, nurse's, or other case manager's workflow. As another example, review of test results is placed in a physician's workflow so that appropriate action may be taken before or after discharge. A blood sample or other test may be performed at discharge, but the results not available before discharge. This may occur, for example, where the predictor identifies a probability of readmission beyond the threshold due to missing information. The test is ordered to provide the missing information. A workflow action is automatically scheduled to examine the test results and take appropriate action to avoid readmission. Similarly, a workflow action may be scheduled during the patient's stay to avoid a higher risk of readmission.

The workflow action item may be generated to review reasons for readmission after readmission. Where a patient is readmitted, a retrospective analysis may be performed in an effort to identify what could or should have been done differently. A case manager, such as an administrator of a hospital, may predict the probability of readmission based on the data at the time of the previous discharge or review the saved probability. The discharge instructions, workflow action items, or other use of the probability may be examined to determine if other action was warranted. Future workflow action items, discharge instructions, physician education, or other actions may be performed to avoid similar reasons for readmission in other patients. A correlation study of readmitted patients may indicate common problems or trends.

The workflow is a separate application that queries the results of the mining and/or prediction of probability of readmission. The workflow uses the results or is included as part of the predictor application. Any now known or later developed software or system providing a workflow engine may be configured to initiate a workflow based on data.

The workflow system may be configured to monitor adherence to the action items. Reminders may be automatically generated where an action item is due or past due so that health care providers are better able to follow the recommendations.

Other predictors or statistical classifiers may be provided. One example predictor is for compliance by the patient with the discharge or other instructions. A level of risk (i.e., risk stratification) and/or reasons for risk are predicted. The ground truth for compliance may rely on patient surveys or questionnaires. The predictor for whether a patient will comply is trained from the training data. Different predictors may be generated for different groups, such as by type of condition. The variables used for training may be the same or different than for training the predictor of readmission. The trained predictor of compliance may have a different or same feature vector as the predictor of readmission. Mining is performed to determine the values for training and/or the values for application.

The predictor for compliance is triggered for application at the time of discharge or when other instructions are given to the patient, but may be performed at other times. The values of variables in the feature vector of the predictor of compliance are input to the predictor. The application of the predictor to the electronic medical record of the patient results in an output probability of compliance by the patient. The reasons for the probability being beyond a threshold or thresholds may also be output, such as a lack of insurance or high medication cost contributing as a strong or stronger link to the probability being beyond the threshold. For example, a patient may be discharged to an unknown location (no home or hospice listed in the discharge location variable). An unknown location may occur for homeless patients whom are less able to adhere to a care plan. The discharge location being unknown may be output so that a care provider may make subsequent care arrangements before discharge or assign a case worker to assist with adherence.

The probability of compliance may be used to modify the discharge or other instructions and/or workflow action items. For example, the type of follow-up may be more intensive or thorough where the probability of compliance is low. As another example, a workflow action may be generated to identify alternative medicines where the cost of medication is high. A consultation with a social worker may be arranged and/or the discharge instructions based on lower cost alternatives may be provided where the patient does not have insurance.

Figure 2:
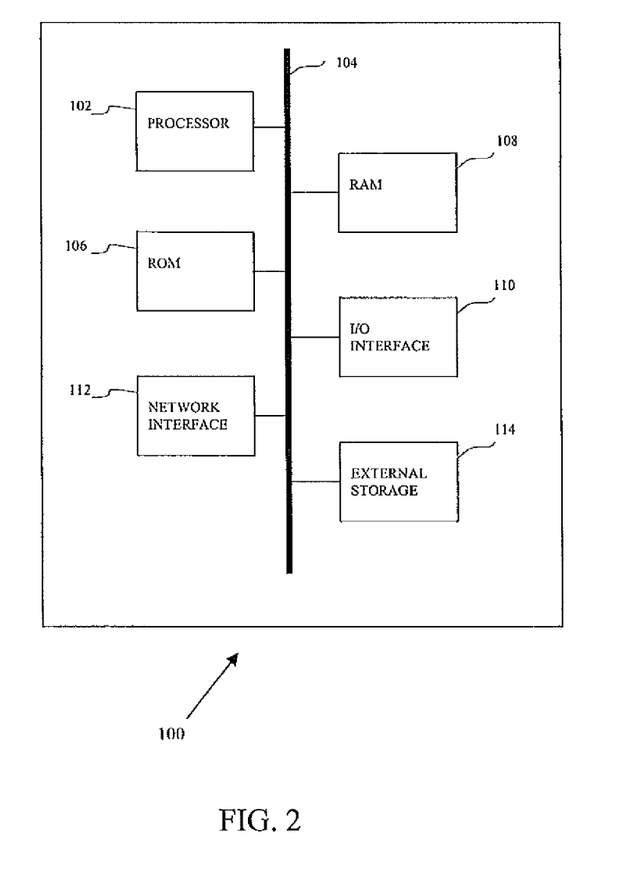
FIG. 2 is a block diagram of one embodiment of a computer processing system for mining patient data and/or using resulting mined data.

FIG. 2 is a block diagram of an example computer processing system 100 for implementing the embodiments described herein, such as preventing hospital or medical entity readmission. The systems, methods and/or computer readable media may be implemented in various forms of hardware, software, firmware, special purpose processors, or a combination thereof. Some embodiments are implemented in software as a program tangibly embodied on a program storage device. By implementing with a system or program, completely or semi-automated workflows, predictions, classifying, and/or data mining are provided to assist a person or medical professional.

The system 100 is for generating a predictor, such as implementing machine learning to train a statistical classifier. Alternatively or additionally, the system 100 is for applying the predictor. The system 100 may also implement associated workflows.

The system 100 is a computer, personal computer, server, PACs workstation, imaging system, medical system, network processor, or other now know or later developed processing system. The system 100 includes at least one processor (hereinafter processor) 102 operatively coupled to other components via a system bus 104. The program may be uploaded to, and executed by, a processor 102 comprising any suitable architecture. Likewise, processing strategies may include multiprocessing, multitasking, parallel processing and the like. The processor 102 is implemented on a computer platform having hardware such as one or more central processing units (CPU), a random access memory (RAM), and input/output (I/O) interface(s). The computer platform also includes an operating system and microinstruction code. The various processes and functions described herein may be either part of the microinstruction code or part of the program (or combination thereof) which is executed via the operating system. Alternatively, the processor 102 is one or more processors in a network and/or on an imaging system.

The processor 102 is configured to learn a classifier, such as creating a predictor of readmission from training data, to mine the electronic medical record of the patient or patients, and/or to apply a machine-learnt classifier to predict the probability of readmission. Training and application of a trained classifier are first discussed below. Example embodiments for mining follow.

For training, the processor 102 determines the relative or statistical contribution of different variables to the outcome, readmission. A programmer may select variables to be considered. The programmer may influence the training, such as assigning limitations on the number of variables and/or requiring inclusion of one or more variables to be used as the input feature vector of the final classifier. By training, the classifier identifies variables contributing to readmission. Where the training data is for patients from a given medical entity, the learning identifies the variables most appropriate or determinative for readmission based on discharge from that medical entity. The training incorporates the variables into a predictor of readmission for a future patient of the medical entity.

For application, the processor 102 applies the resulting (machine-learned) statistical model to the data for a patient. For each patient or for each patient in a category of patients (e.g., patients treated for a specific condition or by a specific group within a medical entity), the predictor is applied to the data for the patient. The values for the identified and incorporated variables of the machine-learnt statistical model are input as a feature vector. A matrix of weights and combinations of weighted values calculates a probability of readmission.

The predictor of readmission may have any accuracy. For example, the receiver operating characteristic (ROC) curve may show an area of about 81% and a standard of deviation of about 1.7% where, at about 0% false alarms, about 70% of the eventual readmissions are predicted. Other performance may be provided.

The processor 102 associates different workflows with different possible predictions of the predictor. The probability of readmission, the probability of compliance, severity, and/or most determinative values may be different for different patients. One or a combination of these factors is used to select an appropriate workflow or action. Different predictions or probabilities of readmission may result in different jobs to be performed and/or different instructions.

The processor 102 is operable to assign actions or to perform workflow actions. For example, the processor 102 initiates contact for follow-up by electronically notifying a patient in response to identifying a probability of readmission. As another example, the processor 102 requests documentation to resolve ambiguities in a medical record. In another example, the processor 102 generates a request for clinical action likely to decrease a probability of readmission. Clinical actions may include a test order, recommended action, request for patient information, other source of obtaining clinical information, or combinations thereof. To decrease a probability of readmission, the processor 102 may generate a prescription form, clinical order (e.g., test order), or other workflow action.

In a real-time usage, the processor 102 receives currently available medical information for a patient. Based on the currently available information and mining the patient record, the processor 102 may indicate how to mitigate risk of readmission. The actions may then be performed during the treatment or before discharge.

The processor 102 implements the operations as part of the system 100 or a plurality of systems. A read-only memory (ROM) 106, a random access memory (RAM) 108, an I/O interface 110, a network interface 112, and external storage 114 are operatively coupled to the system bus 104 with the processor 102. Various peripheral devices such as, for example, a display device, a disk storage device(e.g., a magnetic or optical disk storage device), a keyboard, printing device, and a mouse, may be operatively coupled to the system bus 104 by the I/O interface 110 or the network interface 112.

The computer system 100 may be a standalone system or be linked to a network via the network interface 112. The network interface 112 may be a hard-wired interface. However, in various exemplary embodiments, the network interface 112 may include any device suitable to transmit information to and from another device, such as a universal asynchronous receiver/transmitter (UART), a parallel digital interface, a software interface or any combination of known or later developed software and hardware. The network interface may be linked to various types of networks, including a local area network (LAN), a wide area network (WAN), an intranet, a virtual private network (VPN), and the Internet.

The instructions and/or patient record are stored in a non-transitory computer readable memory, such as the external storage 114. The same or different computer readable media may be used for the instructions and the patient record data. The external storage 114 may be implemented using a database management system (DBMS) managed by the processor 102 and residing on a memory such as a hard disk, RAM, or removable media. Alternatively, the storage 114 is internal to the processor 102 (e.g. cache). The external storage 114 may be implemented on one or more additional computer systems. For example, the external storage 114 may include a data warehouse system residing on a separate computer system, a PACS system, or any other now known or later developed hospital, medical institution, medical office, testing facility, pharmacy or other medical patient record storage system. The external storage 114, an internal storage, other computer readable media, or combinations thereof store data for at least one patient record for a patient. The patient record data may be distributed among multiple storage devices or in one location.

The patient data for training a machine learning classifier is stored. The training data includes data for patients that have been readmitted and data for patients that have not been readmitted after a selected time. The patients are for a same medical entity, group of medical entities, region, or other collection.

Alternatively or additionally, the data for applying a machine-learnt classifier is stored. The data is for a patient being treated or ready for discharge. The memory stores the electronic medical record of one or more patients. Links to different data sources may be provided or the memory is made up of the different data sources. Alternatively, the memory stores extracted values for specific variables.

The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. Because some of the constituent system components and method steps depicted in the accompanying figures are preferably implemented in software, the actual connections between the system components (or the process steps) may differ depending upon the manner in which the present embodiments are programmed.

Figure 4:
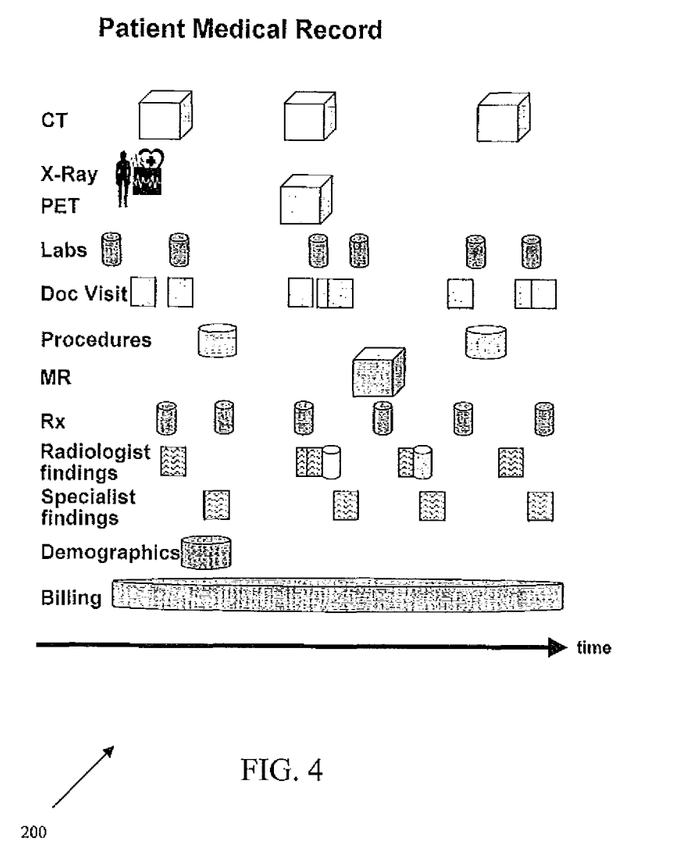
FIG. 4 shows an exemplary computerized patient record (CPR).

Health care providers may employ automated techniques for information storage and retrieval. The use of a computerized patient record (CPR)(e.g., an electronic medical record) to maintain patient information is one such example. As shown in FIG. 4, an exemplary CPR 200 includes information collected over the course of a patient's treatment or use of an institution. This information may include, for example, computed tomography (CT) images, X-ray images, laboratory test results, doctor progress notes, details about medical procedures, prescription drug information, radiological reports, other specialist reports, demographic information, family history, patient information, and billing (financial) information.

A CPR may include a plurality of data sources, each of which typically reflects a different aspect of a patient's care. Alternatively, the CPR is integrated into one data source. Structured data sources, such as financial, laboratory, and pharmacy databases, generally maintain patient information in database tables. Information may also be stored in unstructured data sources, such as, for example, free text, images, and waveforms. Often, key clinical findings are only stored within unstructured physician reports, annotations on images or other unstructured data source.

Referring to FIG. 2, the processor 102 executes the instructions stored in the computer readable media, such as the storage 114. The instructions are for mining patient records (e.g., the CPR), predicting readmission, assigning workflow jobs, other functions, or combinations thereof. For training and/or application of the predictor of readmission, values of variables are used. The values for particular patients are mined from the CPR. The processor 102 mines the data to provide values for the variables.

Figure 3:
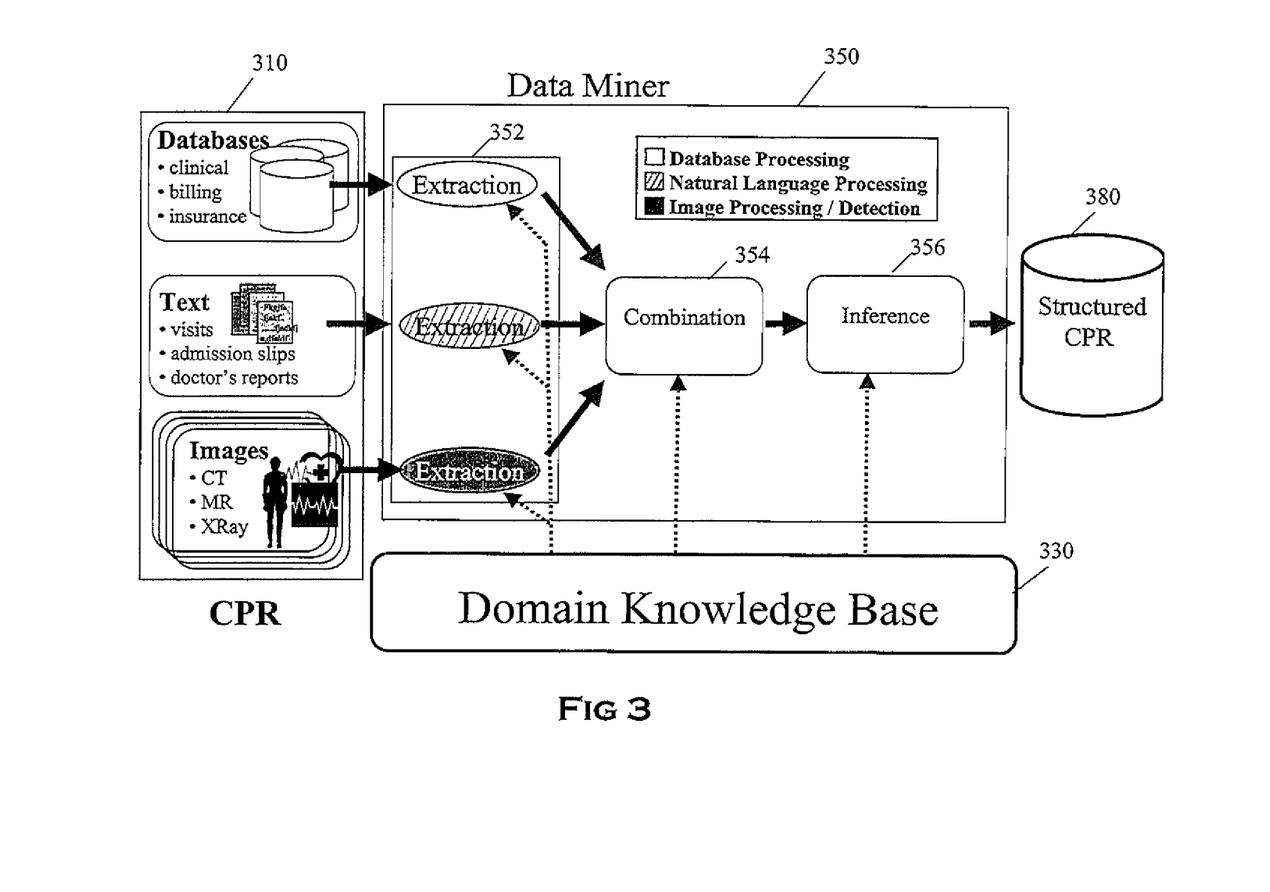
FIG. 3 shows an exemplary data mining framework for mining clinical information.

Any technique may be used for mining the patient record, such as structured data based searching. In one embodiment, the methods, systems and/or instructions disclosed in U.S. Published Application No. 2003/0120458 are used, such as for mining from structured and unstructured patient records. FIG. 3 illustrates an exemplary data mining system implemented by the processor 102 for mining a patient record to create high-quality structured clinical information. The processing components of the data mining system are software, firmware, microcode, hardware, combinations thereof, or other processor based objects. The data mining system includes a data miner 350 that mines information from a CPR 310 using domain-specific knowledge contained in a knowledge base 330. The data miner 350 includes components for extracting information from the CPR 352, combining all available evidence in a principled fashion over time 354, and drawing inferences from this combination process 356. The mined information may be stored in a structured CPR 380. The architecture depicted in FIG. 4 supports plug-in modules wherein the system may be easily expanded for new data sources, diseases, and hospitals. New element extraction algorithms, element combining algorithms, and inference algorithms can be used to augment or replace existing algorithms.

The mining is performed as a function of domain knowledge. The domain knowledge provides an indication of reliability of a value based on the source or context. For example, a note indicating the patient is a smoker may be accurate 90% of the time, so a 90% probability is assigned. A blood test showing nicotine may indicate that the patient is a smoker with 60% accuracy.

Detailed knowledge regarding the domain of interest, such as, for example, a disease of interest, guides the process to identify relevant information. This domain knowledge base 330 can come in two forms. It can be encoded as an input to the system, or as programs that produce information that can be understood by the system. For example, a study determines factors contributing to readmission. These factors and their relationships may be used to mine for values. The study is used as domain knowledge for the mining. Additionally or alternatively, the domain knowledge base 330 may be learned from test data.

The domain-specific knowledge may also include disease-specific domain knowledge. For example, the disease-specific domain knowledge may include various factors that influence risk of a disease, disease progression information, complications information, outcomes, and variables related to a disease, measurements related to a disease, and policies and guidelines established by medical bodies.

The information identified as relevant by the study, guidelines for treatment, medical ontologies, or other sources provides an indication of probability that a factor or item of information indicates or does not indicate a particular value of a variable. The relevance may be estimated in general, such as providing a relevance for any item of information more likely to indicate a value as 75% or other probability above 50%. The relevance may be more specific, such as assigning a probability of the item of information indicating a particular diagnosis based on clinical experience, tests, studies or machine learning. Based on the domain-knowledge, the mining is performed as a function of existing knowledge, guidelines, or best practices regarding readmissions. The domain knowledge indicates elements with a probability greater than a threshold value of indicating the patient state (i.e., collection of values). Other probabilities may be associated with combinations of information.

Domain-specific knowledge for mining the data sources may include institution-specific domain knowledge. For example, information about the data available at a particular hospital, document structures at a hospital, policies of a hospital, guidelines of a hospital, and any variations of a hospital. The domain knowledge guides the mining, but may guide without indicating a particular item of information from a patient record.

The extraction component 352 deals with gleaning small pieces of information from each data source regarding a patient or plurality of patients. The pieces of information or elements are represented as probabilistic assertions about the patient at a particular time. Alternatively, the elements are not associated with any probability. The extraction component 352 takes information from the CPR 310 to produce probabilistic assertions (elements) about the patient that are relevant to an instant in time or period. This process is carried out with the guidance of the domain knowledge that is contained in the domain knowledge base 330. The domain knowledge for extraction is generally specific to each source, but may be generalized.

The data sources include structured and/or unstructured information. Structured information may be converted into standardized units, where appropriate. Unstructured information may include ASCII text strings, image information in DICOM (Digital Imaging and Communication in Medicine) format, and text documents partitioned based on domain knowledge. Information that is likely to be incorrect or missing may be noted, so that action may be taken. For example, the mined information may include corrected information, including corrected ICD-9 diagnosis codes.

Extraction from a database source may be carried out by querying a table in the source, in which case, the domain knowledge encodes what information is present in which fields in the database. On the other hand, the extraction process may involve computing a complicated function of the information contained in the database, in which case, the domain knowledge may be provided in the form of a program that performs this computation whose output may be fed to the rest of the system.

Extraction from images, waveforms, etc., may be carried out by image processing or feature extraction programs that are provided to the system.

Extraction from a text source may be carried out by phrase spotting, which requires a list of rules that specify the phrases of interest and the inferences that can be drawn there from. For example, if there is a statement in a doctor's note with the words "There is evidence of metastatic cancer in the liver," then, in order to infer from this sentence that the patient has cancer, a rule is needed that directs the system to look for the phrase "metastatic cancer," and, if it is found, to assert that the patient has cancer with a high degree of confidence (which, in the present embodiment, translates to generate an element with name "Cancer", value "True" and confidence 0.9).

The combination component 354 combines all the elements that refer to the same variable at the same time period to form one unified probabilistic assertion regarding that variable. Combination includes the process of producing a unified view of each variable at a given point in time from potentially conflicting assertions from the same/different sources. These unified probabilistic assertions are called factoids. The factoid is inferred from one or more elements. Where the different elements indicate different factoids or values for a factoid, the factoid with a sufficient (thresholded) or highest probability from the probabilistic assertions is selected. The domain knowledge base may indicate the particular elements used. Alternatively, only elements with sufficient determinative probability are used. The elements with a probability greater than a threshold of indicating a patient state (e.g., directly or indirectly as a factoid), are selected. In various embodiments, the combination is performed using domain knowledge regarding the statistics of the variables represented by the elements ("prior probabilities").

The patient state is an individual model of the state of a patient. The patient state is a collection of variables that one may care about relating to the patient, such as established by the domain knowledgebase. The information of interest may include a state sequence, i.e., the value of the patient state at different points in time during the patient's treatment.

The inference component 356 deals with the combination of these factoids, at the same point in time and/or at different points in time, to produce a coherent and concise picture of the progression of the patient's state over time. This progression of the patient's state is called a state sequence. The patient state is inferred from the factoids or elements. The patient state or states with a sufficient (thresholded), high probability or highest probability is selected as an inferred patient state or differential states.

Inference is the process of taking all the factoids and/or elements that are available about a patient and producing a composite view of the patient's progress through disease states, treatment protocols, laboratory tests, clinical action or combinations thereof. Essentially, a patient's current state can be influenced by a previous state and any new composite observations. The risk for readmission may be considered as a patient state so that the mining determines the risk without a further application of a separate model.

The domain knowledge required for this process may be a statistical model that describes the general pattern of the evolution of the disease of interest across the entire patient population and the relationships between the patient's disease and the variables that may be observed (lab test results, doctor's notes, or other information). A summary of the patient may be produced that is believed to be the most consistent with the information contained in the factoids, and the domain knowledge.

For instance, if observations seem to state that a cancer patient is receiving chemotherapy while he or she does not have cancerous growth, whereas the domain knowledge states that chemotherapy is given only when the patient has cancer, then the system may decide either: (1) the patient does not have cancer and is not receiving chemotherapy (that is, the observation is probably incorrect), or (2) the patient has cancer and is receiving chemotherapy (the initial inference—that the patient does not have cancer—is incorrect); depending on which of these propositions is more likely given all the other information. Actually, both (1) and (2) may be concluded, but with different probabilities.

As another example, consider the situation where a statement such as "The patient has metastatic cancer" is found in a doctor's note, and it is concluded from that statement that <cancer=True (probability=0.9)>. (Note that this is equivalent to asserting that <cancer=True (probability=0.9), cancer=unknown (probability=0.1)>).

Now, further assume that there is a base probability of cancer <cancer=True (probability=0.35), cancer=False (probability=0.65)>(e.g., 35% of patients have cancer). Then, this assertion is combined with the base probability of cancer to obtain, for example, the assertion <cancer=True (probability=0.93), cancer=False (probability=0.07)>.

Similarly, assume conflicting evidence indicated the following:
1. <cancer=True (probability=0.9), cancer=unknown probability=0.1)>
2. <cancer=False (probability=0.7), cancer=unknown (probability=0.3)>
3. <cancer =True (probability=0.1), cancer=unknown (probability=0.9)>and
4. <cancer=False (probability=0.4), cancer=unknown (probability=0.6)>.

In this case, we might combine these elements with the base probability of cancer <cancer=True (probability=0.35), cancer=False (probability=0.65)>to conclude, for example, that <cancer=True (prob=0.67), cancer=False (prob=0.33)>.

Numerous data sources may be assessed to gather the elements, and deal with missing, incorrect, and/or inconsistent information. As an example, consider that, in determining whether a patient has diabetes, the following information might be extracted:
(a) ICD-9 billing codes for secondary diagnoses associated with diabetes;
(b) drugs administered to the patient that are associated with the treatment of diabetes (e.g., insulin);
(c) patient's lab values that are diagnostic of diabetes (e.g., two successive blood sugar readings over 250 mg/d);
(d) doctor mentions that the patient is a diabetic in the H&P (history & physical) or discharge note (free text); and
(e) patient procedures (e.g., foot exam) associated with being a diabetic.

As can be seen, there are multiple independent sources of information, observations from which can support (with varying degrees of certainty) that the patient is diabetic (or more generally has some disease/condition). Not all of them may be present, and in fact, in some cases, they may contradict each other. Probabilistic observations can be derived, with varying degrees of confidence. Then these observations (e.g., about the billing codes, the drugs, the lab tests, etc.) may be probabilistically combined to come up with a final probability of diabetes. Note that there may be information in the patient record that contradicts diabetes. For instance, the patient has some stressful episode (e.g., an operation) and his blood sugar does not go up.

The above examples are presented for illustrative purposes only and are not meant to be limiting. The actual manner in which elements are combined depends on the particular domain under consideration as well as the needs of the users of the system. Further, while the above discussion refers to a patient-centered approach, actual implementations may be extended to handle multiple patients simultaneously. Additionally, a learning process may be incorporated into the domain knowledge base 330 for any or all of the stages (i.e., extraction, combination, inference).

The system may be run at arbitrary intervals, periodic intervals, or in online mode. When run at intervals, the data sources are mined when the system is run. In online mode, the data sources may be continuously mined. The data miner may be run using the Internet. The created structured clinical information may also be accessed using the Internet. Additionally, the data miner may be run as a service. For example, several hospitals may participate in the service to have their patient information mined, and this information may be stored in a data warehouse owned by the service provider. The service may be performed by a third party service provider (i.e., an entity not associated with the hospitals).

Once the structured CPR 380 is populated with patient information, it will be in a form where it is conducive for answering questions regarding individual patients, and about different cross-sections of patients. The values are available for use in predicting readmission.

The domain knowledgebase, extractions, combinations and/or inference may be responsive or performed as a function of one or more variables. For example, the probabilistic assertions may ordinarily be associated with an average or mean value. However, some medical practitioners or institutions may desire that a particular element be more or less indicative of a patient state. A different probability may be associated with an element. As another example, the group of elements included in the domain knowledge base for a predictor of readmission may be different for different medical entities. The threshold for sufficiency of probability or other thresholds may be different for different people or situations.

Other variables may be use or institution specific. For example, different definitions of a primary care physician may be provided. A number of visits threshold may be used, such as visiting the same doctor 5 times indicating a primary care physician. A proximity to a patient's residence may be used. Combinations of factors may be used.

The user may select different settings. Different users in a same institution or different institutions may use different settings. The same software or program operates differently based on receiving user input. The input may be a selection of a specific setting or may be selection of a category associated with a group of settings.

The mining, such as the extraction, and/or the inferring, such as the combination, are performed as a function of the selected threshold. By using a different upper limit of normal for the patient state, a different definition of information used in the domain knowledge or other threshold selection, the patient state or associated probability may be different. User's with different goals or standards may use the same program, but with the versatility to more likely fulfill the goals or standards.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A system for predicting or preventing hospital readmission, the system comprising:
   at least one memory operable to store data for a plurality of readmitted patients of a first hospital; and
   a first processor configured to:
      identify variables contributing to readmission for the first hospital based on the data for the plurality of the readmitted patients of the first hospital; and
      incorporate the variables into a predictor of readmission for a future patient of the first hospital;
      wherein the processor is configured to identify and incorporate by machine learning a statistical model from the data, the predictor comprising a matrix of the statistical model.

2. The system of claim 1 wherein the processor is configured to mine the data including mining unstructured information, the mining providing values for the variables, the values inferred from different possible values in the data and probabilities assigned to the possible values.

3. The system of claim 1 wherein the processor is configured to associate different workflows with different possible predictions of the predictor.

4. In a non-transitory computer readable storage medium having stored therein data representing instructions executable by a programmed processor for predicting or preventing hospital readmission, the storage medium comprising instructions for:
   predicting a probability of readmission of a patient, the predicting occurring during a patient stay;
   comparing the probability to a threshold; and
   generating an alert based on the comparing, the generating occurring during the patient stay;
   wherein generating the alert comprises displaying the alert on a display while preventing entry of information until occurrence of an event such that the preventing is temporary, is until the probability is reduced, or is until overridden.

5. The non-transitory computer readable storage medium of claim 4 wherein generating the alert also comprises transmitting a message to a cellular phone.

6. The non-transitory computer readable storage medium of claim 4 wherein generating the alert comprises displaying the alert on a bedside monitor of the patient.

7. The non-transitory computer readable storage medium of claim 4 wherein generating the alert comprises alerting a person with a notice indicating the patient and an indication of risk of the readmission.

8. The non-transitory computer readable storage medium of claim 4 further comprising;
   receiving an indication of an event for a patient from a hospital;
   triggering application of a predictor of readmission in response to the receiving of the indication;
   wherein predicting comprises applying the predictor of the readmission to an electronic medical record of the patient in response to the triggering, the predictor being based on readmission data of the hospital, the probability being based on the applying of the predictor to the electronic medical record of the patient.

9. The method of claim 8 further comprising:
mining the electronic medical record of the patient; and
populating a feature vector used for predicting the probability from the mining;
wherein applying the predictor comprises applying the predictor to the feature vector.

10. The non-transitory computer readable storage medium of claim 9 wherein mining comprises mining from a first data source of the electronic medical record and mining from a second data source of the electronic medical record, the first data source comprising structured data and the second data source comprising unstructured data, the mining outputting values for the feature vector in a structured format from the first and second data sources.

11. The non-transitory computer readable storage medium of claim 9 wherein mining comprises inferring a value for each of a plurality of variables, each value inferred by probabilistic combination of probabilities associated with different possible values from different sources, the inferred values for the variables comprising the feature vector.

12. The non-transitory computer readable storage medium of claim 9 where mining comprises mining as a function of existing knowledge, guidelines, best practices, or about specific institutions regarding readmissions.

13. The non-transitory computer readable storage medium of claim 4 further comprising:
automatically scheduling a job entry in a workflow of a case manager, the job entry being for examination to avoid readmission.

14. The non-transitory computer readable storage medium of claim 8 wherein applying the predictor comprises applying a machine-learnt classifier, and wherein predicting comprises obtaining an output of the machine-learnt classifier, the machine-learnt classifier comprising a statistical model.

15. The non-transitory computer readable storage medium of claim 4 wherein generating the alert comprises outputting at least one variable having a value for the patient associated with a strongest link to the probability indicating a risk of readmission, the strongest link being relative to links for other values of other variables to the risk.

16. The non-transitory computer readable storage medium of claim 4 wherein generating the alert comprises outputting a mitigation plan associated with the predicting.

17. The non-transitory computer readable storage medium of claim 4 wherein generating the alert comprises outputting based on a criteria set for the hospital.

18. The non-transitory computer readable storage medium of claim 4 wherein generating the alert comprises outputting instructions based on the probability.

19. The non-transitory computer readable storage medium of claim 18 further comprising:
applying a predictor of compliance by the patient with the instructions to an electronic medical record of the patient; and
predicting a probability of compliance of the patient based on the applying of the predictor of compliance.

20. The non-transitory computer readable storage medium of claim 4 wherein preventing comprises preventing being limited to a type of the information.

* * * * *